United States Patent
Gould

[11] Patent Number: 5,766,141
[45] Date of Patent: Jun. 16, 1998

[54] WRIST BRACE FOR CARPAL TUNNEL SYNDROME PREVENTION AND TREATMENT

[76] Inventor: David Gould, 140 Ample Way, Shepherdsville, Ky. 40165

[21] Appl. No.: 744,781

[22] Filed: Nov. 6, 1996

[51] Int. Cl.[6] .................................................. A61F 13/00
[52] U.S. Cl. ........................... 602/21; 602/6; 602/20
[58] Field of Search ............................. 602/6–11, 18, 602/20–22, 27, 60–62, 64, 65; 128/878, 879, 882; 601/33, 40; 2/20, 21

[56] References Cited

U.S. PATENT DOCUMENTS

| | | | |
|---|---|---|---|
| 3,682,163 | 8/1972 | Plummer | 602/6 |
| 3,788,307 | 1/1974 | Kistner. | |
| 4,143,653 | 3/1979 | Wichman | 602/22 |
| 4,382,439 | 5/1983 | Shen. | |
| 4,424,809 | 1/1984 | Yonvankin | 602/62 |
| 4,766,890 | 8/1988 | Hollrah. | |
| 4,782,825 | 11/1988 | Lonardo. | |
| 5,160,314 | 11/1992 | Peters. | |
| 5,230,698 | 7/1993 | Garth | 602/18 |
| 5,366,438 | 11/1994 | Martin, Sr. | 602/18 |
| 5,376,066 | 12/1994 | Phillips et al. . | |
| 5,397,296 | 3/1995 | Sydor et al. . | |
| 5,417,645 | 5/1995 | Lemmen. | |

*Primary Examiner*—Richard J. Apley
*Assistant Examiner*—Denise Pothier
*Attorney, Agent, or Firm*—Middleton & Reutlinger; Charles G. Lamb

[57] ABSTRACT

A wrist brace for correction of carpal tunnel syndrome and prevention thereof includes an elongated, flexible resilient member having a plurality of outwardly extending lips along an upper side portion of the flexible member. The outwardly extending lips are of preselected heights and lengths and at preselected positions to provide strategically located leverage and pressure points to relieve the restriction of the medial nerve and allows for substantially the normal use of the hand and wrist in a work or sport environment.

8 Claims, 3 Drawing Sheets

1

WRIST BRACE FOR CARPAL TUNNEL SYNDROME PREVENTION AND TREATMENT

BACKGROUND OF THE INVENTION

The present invention relates to support devices for treatment and prevention of carpal tunnel syndrome and more particularly to a wrist brace for carpal tunnel syndrome which can be worn without interfering with the movement of the hand and fingers of the wrist brace wearer.

Carpal tunnel syndrome is a painful condition caused by excessive pressure and stress on the medial nerve that runs through the wrist. Excess pressure and stress is usually caused by repetitive use of the hands and wrists in a working or sports environment. Once the symptoms of pain, numbness and tingling and lack of strength appear in the wrist, the carpal tunnel syndrome worsens and if not treated or the wrist and adjoining hand are not rested for a sufficient period of time, usually a period of several days in order to let the medial nerve heal, permanent damage of the nerve may occur. And, many jobs subject workers to stressful anterior pressure of the wrist. Over the last few years, and particularly with the emphasis on the use of computers in the work place, many workers spend entire work days at computers continually manipulating their fingers, hands and wrists. Thus, the number of persons experiencing carpal tunnel syndrome has been on a steady rise.

There have been a number of proposals in the prior art dealing with carpal tunnel syndrome which are intended to provide treatment or to relieve some of the pressure and stress upon the medial nerve. Most of the devices proposed have included wrist splints and braces which are to prevent the stress and pressure on the medial nerve and in most instances the devices immobilize the thumb, wrist and hand and therefore the person suffering the carpal tunnel syndrome has limited, if any, use of the hand that is effected with wearing these devices.

SUMMARY OF THE INVENTION

It is an object of the present invention to provide a wrist brace for prevention of carpal tunnel syndrome.

It is another object of the present invention to correct existing carpal tunnel syndrome.

It is even another object of the present invention to provide a wrist brace for protection against reoccurrence of carpal tunnel syndrome, which does not interfere with the use of the wrist and hand of the wearer thereby allowing continuance of his normal duties.

It is also an object of the present invention to provide a wrist brace for carpal tunnel syndrome that provides for proper functional mechanics of the normal hand and wrist movement with strategically located leverage and pressure to relocate the carpals, radius and ulna.

It is a further object of the present invention to provide a wrist brace for carpal tunnel syndrome which provides for a combination of leverage, traction and approximation of the ulna and radius thereby relieving the restriction of the medial nerve which is the result of carpal tunnel syndrome.

More particularly, the present invention provides a wrist brace for carpal tunnel syndrome comprising an elongated resiliently flexible member having an upper elongated side portion with a plurality of outwardly turned lips along the upper elongated side portion, and opposed ends with adjustable fastening means to fasten said ends to each other thereby forming a circumferential enclosure for wrists of varying diameters.

Other objects and advantages of the present invention will be readily appreciated with the understanding of the preferred embodiments of the present invention as set forth hereinafter in the specification taken in connection with the accompanying drawings.

DETAILED DESCRIPTION OF THE PREFERRED EMBODIMENTS

Figure 1:
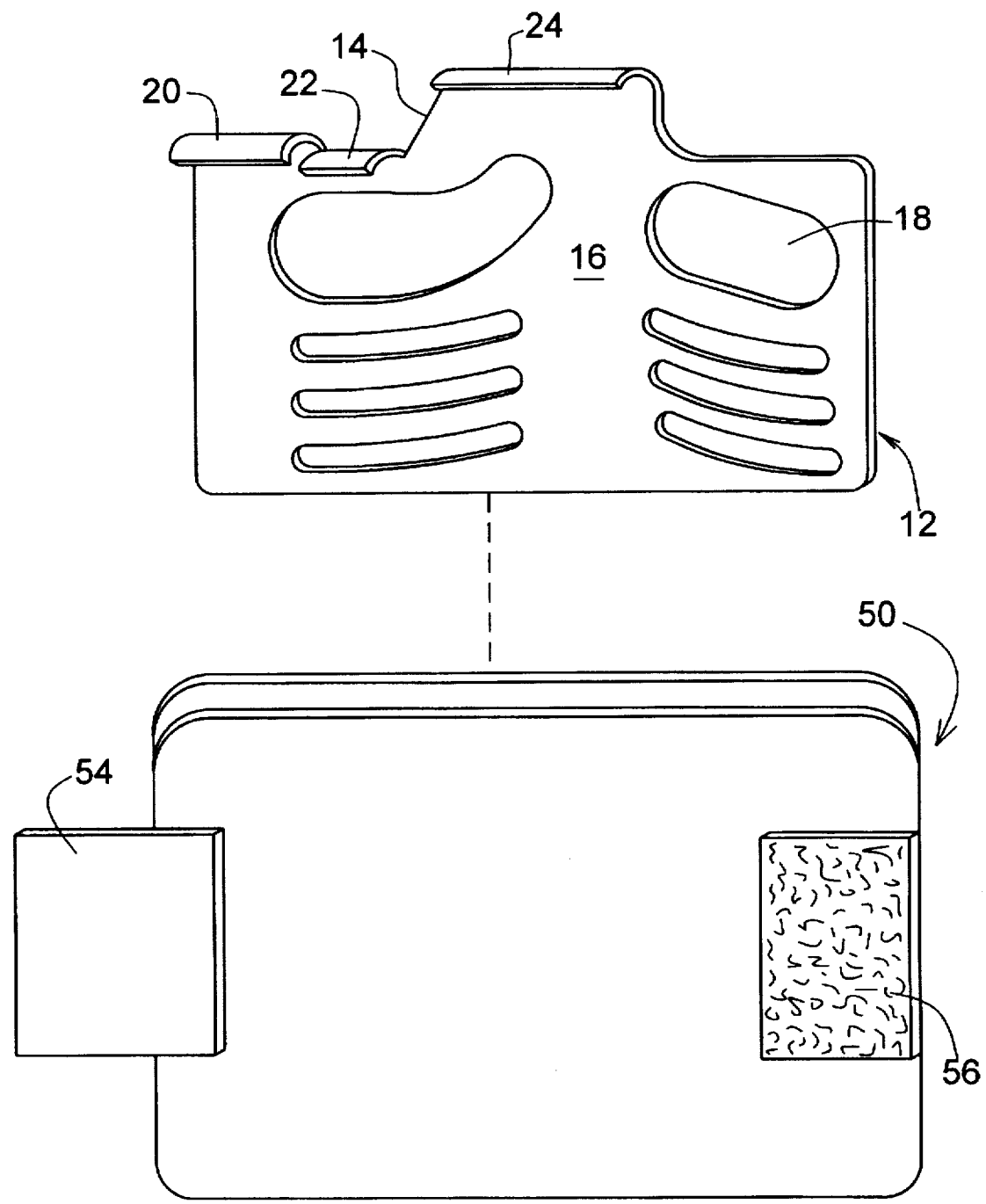
FIG. 1 is an exploded perspective view of one wrist brace of the present invention.
Figure 3:
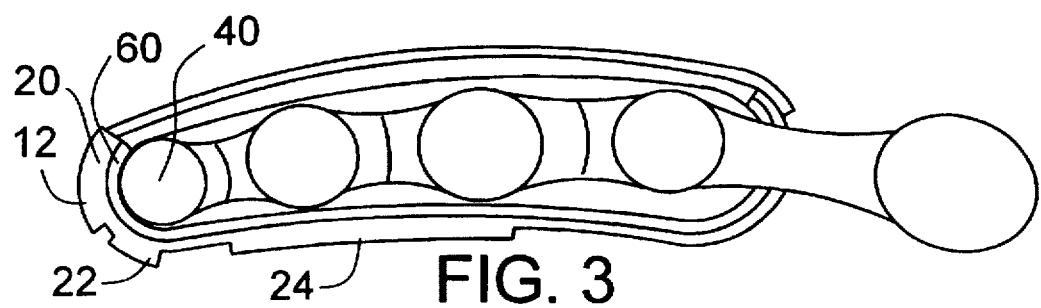
FIG. 3 is a top view of the wrist brace of FIG. 2 shown in a use condition around the hand of a user; and, FIG. 4 is a side view of the wrist brace and hand of FIG. 3.
Figure 4:
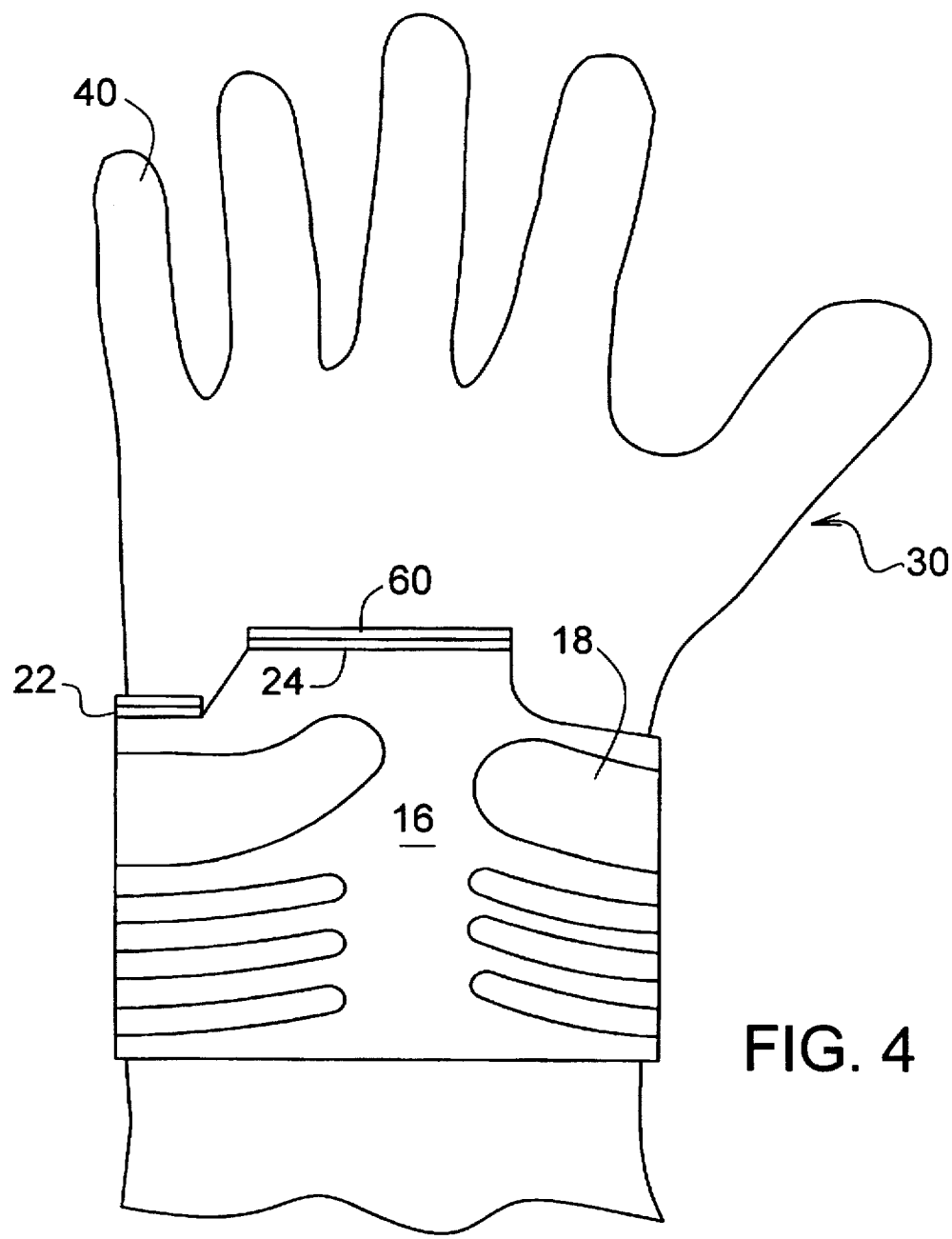

Shown in FIG. 1 is a wrist brace of the present invention for use with the left hand and wrist which includes an elongated member 12 fabricated from any resilient, flexible material, such as a plastic, which returns to its initial position in a spring-like manner. Moreover, the edges of the elongated member 12 are generally rounded to promote comfort of the wearer when in a use condition and the resilient bias or memory position of the flexible member 12 provides an increased resistance to the movement of the hand at the wrist in either up, down and outward directions as discussed hereinafter. The flexible member 12 is provided with an upper side portion 14 which includes a plurality of lips 20, 22 and 24 which are positioned at specific locations and an outer surface 16. A plurality of openings 18 are provided therein which provide for the flow of air therethrough and prevent restriction or irritation of radius and ulna as well as the evaporation of moisture from the hand and wrist of a user when in a use condition. The openings also provide mobility of the carpal, radius and ulna. As further shown in FIG. 1, cover 50 is also provided with hook and loop fastener strips, such as VELCRO strips or other fastening devices 54, 56, which are used for enclosing the wrist and a portion of a hand in a use position, as shown in FIGS. 3 and 4. The cover 50 is generally of a soft flexible fabric or foam which provides comfort to the wearer so that the wearer of the wrist brace does not come into direct contact with the relatively hard flexible plastic material.

Figure 2:
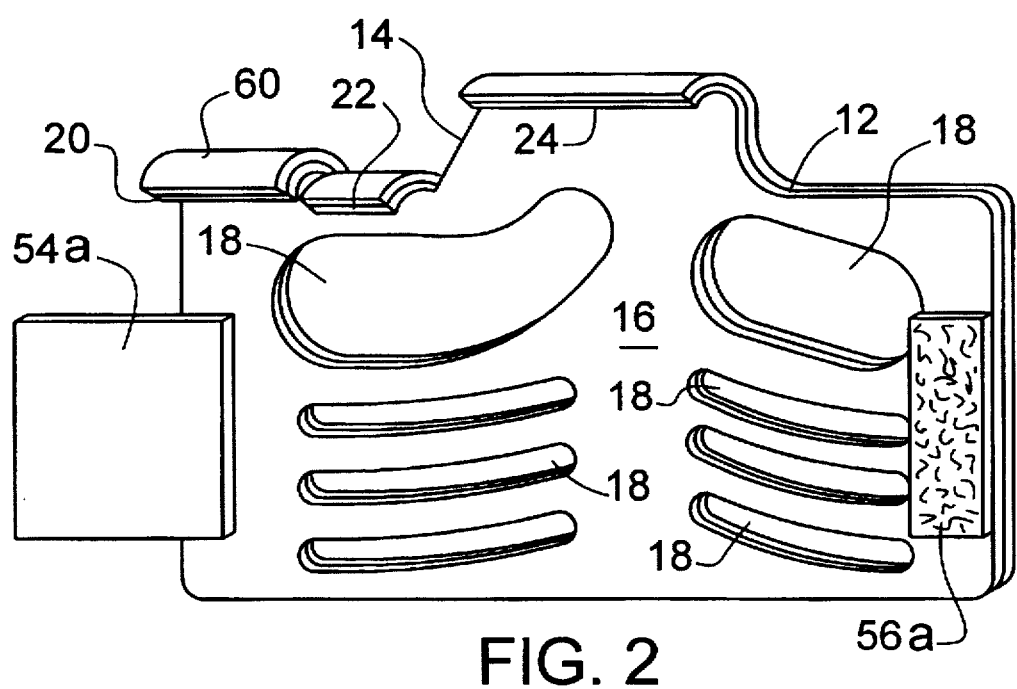
FIG. 2 is a perspective view of another embodiment of a wrist brace of the present invention.

Shown in FIG. 2 is another preferred embodiment of the present invention wherein the elongated flexible resilient member 12 is coated on its inner surface with a soft fabric or foam material identified by the numeral 60. The soft fabric or foam material provides padding between the elongated member 12 and the hand and wrist of the user. Moreover, fastening strips identified by numerals 54a, 56a, are attached directly to the outer surface 16 of the elongated flexible plastic material 12.

Referring back to FIGS. 1 and 2, the outwardly curved lips 20, 22 and 24 along the upper side portion 14 of the elongated member 12 are of preselected height and length to correspond to their eventual position along the wrist and hand of a user when in a use condition. The first or outermost lip 20 is at a position at the left end of the upper side portion, as best shown in FIG. 3, as corresponding to an inner portion of the left hand adjacent to and just below the outer or little finger 40 on a left hand 30. For a right hand, the first or outermost lip 20 is at a position at the right end of the upper side portion. The second or immediate lip 22 is positioned adjacent to the outer lip 20 but at a position generally about a quarter of an inch less in height than the outer lip 20 and along the outer extremity of the hand 30 and along the back side of the hand a selected distance below the outer or little finger 40. The third or innermost lip 24 is adjacent to the second lip 22 and is generally positioned approximately a half of an inch above the second lip 22 and extends along the back portion of the hand 30.

The flexible member 12, positioned as described and shown in FIGS. 3 and 4, prevents the movement of the hand and wrist in deviations from the normal anatomical position of the wrist or hand. Such movements are met with an increased resistance or force by the wrist brace. Moreover, the positioning of the lips 20, 22 and 24, as described hereinbefore, provides for stretching of the hand and wrist at these specific positions so that the hand and wrist are stretched thereby relieving pressure on the medial nerve associated with carpal tunnel syndrome. Thus, the wrist brace when in a proper position is easily attached by the user and is comfortable for use in a work environment and allows near normal hand and wrist function.

It is realized that the embodiment shown and described is useful for the left hand and wrist, but a mirror image of the wrist brace shown in the Figures is incorporated herein for use with the right hand and wrist. It is also realized that other variations and modifications of the preferred embodiment are possible without departing from the scope and spirit of the present invention. And, it is not intended that the aforementioned discussion in any way limit the scope of the present invention as set forth in the appended claims.

What is claimed is:

1. A wrist brace comprising:
    an elongated resilient flexible member having an upper elongated side portion with a plurality of preformed outwardly turned lips along said upper elongated side portion, said elongated resilient flexible member having opposed ends with adjustable fastening means to fasten said ends to each other thereby forming a circumferential enclosure of varying diameters configured to surround the wrist of a user, said plurality of lips including three lips, a first lip being adjacent one end of said upper side portion, a second lip positioned between said first lip and an opposite end of said upper side portion, and a third lip between said second lip and said opposite end of said upper side portion, each of said lips being of a different preselected length.

2. The wrist brace of claim 1, said first lip being adjacent a right end of said upper side portion on a right-handed brace.

3. The wrist brace of claim 1, said first lip being adjacent a left end of said upper side portion on a left-handed brace.

4. The wrist brace of claim 1, said first lip being of a first preselected length, said second lip being of a second preselected length, said second preselected length being less than said first preselected length, and, said third lip being of a third preselected length, said third preselected length being greater than said first preselected length.

5. The wrist brace of claim 4, said first lip being positioned at a first preselected height, said second lip being positioned at a second preselected height, said second preselected height being less than said first preselected height, and, said third lip being positioned at a third preselected height, said third preselected height being greater than said first preselected height.

6. The wrist brace of claim 5, said first preselected height being about one quarter of an inch greater than said second preselected height, and said third preselected height being about one half of an inch greater than said second preselected height.

7. The wrist brace of claim 1 including a cover over said elongated resilient, flexible member, said fastening means being attached to said cover.

8. The wrist brace of claim 1, said elongated resilient, flexible member having an inner surface, said inner surface lined with a soft material, said soft material being selected from the group consisting of a soft fabric or a foam material.

\* \* \* \* \*